United States Patent
Okuda et al.

(10) Patent No.: US 7,867,771 B2
(45) Date of Patent: Jan. 11, 2011

(54) REAGENT FOR MEASURING CLOTTING TIME AND METHOD FOR STABILIZING TISSUE FACTOR

(75) Inventors: Masahiro Okuda, Kobe (JP); Kazuyo Yoshida, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 12/057,812

(22) Filed: Mar. 28, 2008

(65) Prior Publication Data

US 2008/0241941 A1 Oct. 2, 2008

(30) Foreign Application Priority Data

Mar. 28, 2007 (JP) ............................. 2007-085578

(51) Int. Cl.
*G01N 33/86* (2006.01)
*G01N 1/00* (2006.01)

(52) U.S. Cl. .......................... 436/69; 436/63; 436/73; 436/84; 436/174; 436/176; 435/13; 600/369; 73/64.41

(58) Field of Classification Search ............... 436/8, 436/15, 18, 63, 69, 73, 84, 174, 176; 252/408.1; 435/13; 600/369; 73/64.41
See application file for complete search history.

(56) References Cited

U.S. PATENT DOCUMENTS

| 5,017,556 A * | 5/1991 | O'Brien et al. ............... 514/2 |
| 6,670,445 B2 | 12/2003 | Okuhira |
| 6,733,985 B1 * | 5/2004 | Lee ............................. 435/13 |
| 2005/0202509 A1 * | 9/2005 | Okuda et al. ................. 435/7.1 |
| 2008/0124704 A1 | 5/2008 | Okuda et al. |
| 2008/0260858 A1 * | 10/2008 | Morrissey et al. ........... 424/638 |

FOREIGN PATENT DOCUMENTS

| EP | 1074615 A | 2/2001 |
| EP | 1 935 902 A1 | 6/2008 |
| JP | 11160320 * | 6/1999 |
| JP | 2001-255332 A | 9/2001 |
| WO | 03066681 A | 8/2003 |
| WO | 2004082708 A | 9/2004 |
| WO | 2006088741 A | 8/2006 |
| WO | 2007002709 A | 1/2007 |

OTHER PUBLICATIONS

Masato Okada, et al., "Protein Experimental Note (Upper Volume) Extraction and Separation / Purification", Yodosha, Sep. 2006, p. 24.

* cited by examiner

*Primary Examiner*—Maureen M Wallenhorst
(74) *Attorney, Agent, or Firm*—Sughrue Mion, PLLC

(57) ABSTRACT

The present invention provides a reagent for measuring clotting time including a nonionic surfactant, a nickel ion and a tissue factor. A method for stabilizing a tissue factor, and use of a nonionic surfactant and a nickel salt for stabilizing a tissue factor are also disclosed.

8 Claims, 3 Drawing Sheets

REAGENT FOR MEASURING CLOTTING TIME AND METHOD FOR STABILIZING TISSUE FACTOR

FIELD OF THE INVENTION

The present invention relates to a reagent for measuring clotting time comprising a tissue factor and a method for stabilizing a tissue factor.

BACKGROUND

The tissue factor is a start factor related to an extrinsic clotting factor of a blood clotting factor. This tissue factor is one of major components in a reagent for measuring clotting time such as in measurement of prothrombin time. Accordingly, the tissue factor is widely used in clinical diagnosis of abnormality of blood clotting ability.

The tissue factor used as a material of a reagent for measuring clotting time is generally a tissue factor extracted from the brain of cattle, a rabbit or the like. However, a natural tissue factor extracted from such animal brain contains impurities such as blood components, lipoproteins and plasma proteins. Accordingly, when stored for a long time, there is a problem of poor stability to generate precipitates of insoluble materials.

When the naturally derived tissue factor is used as a material of the reagent for measuring clotting time, for improving the stability, proteins such as bovine serum albumin (BSA) and Crystalline (Amano Pharmaceutical Co., Ltd.) and stabilizers such as a surfactant and a highly concentrated glycerin solution are added to the reagent, or the naturally derived tissue factor is partially purified by antibody column chromatography or gel filtration chromatography. However, when a stabilizer such as BSA is added to the reagent, the stabilizer may affect on measuring clotting time. In partial purification, there is a problem that time and costs are required for preparing a large amount of the tissue factor.

With the recent advance of genetic recombination techniques with *Escherichia coli*, yeast etc. as the host, a genetic recombinant human tissue factor and a genetic recombinant rabbit tissue factor have become commercially available.

However, even if the genetic recombinant tissue factor is used as a material of the reagent, its solution may be liable to denature the protein and to reduce the biological activity depending on its state during storage, and as a consequence, there is a problem of poor storage stability.

A nickel compound-containing reagent for measuring clotting time (JP-A 2001-255332) has already been reported. However, this technique is related to a technique of improving the sensitivity and accuracy of clotting time measurement. Accordingly, there is no description of the stabilization of the reagent for measuring clotting time, particularly the stabilization of the tissue factor.

Generally, a heavy metal such as nickel is known to destabilize a protein. Accordingly, the addition of a chelating agent such as EDTA to a solution containing a protein such as an enzyme is known to remove the influence of a heavy metal (Masato Okada et al., Protein Experimental Note (Upper Volume) Extraction and Separation/Purification, Yodosha, p 24, Sep. 10, 1996). The peroxidation, oxidation and denaturation of a protein by the catalytic action of a heavy metal ion can be prevented by the chelating agent. In addition, hydrolysis with a metalloprotease present in a very small amount in a solution is inhibited by the chelating agent.

SUMMARY

The scope of the present invention is defined solely by the appended claims, and is not affected to any degree by the statements within this summary.

The object of the present invention is to provide a reagent for measuring clotting time comprising a stable tissue factor and a method for stabilizing a tissue factor.

DETAILED DESCRIPTION OF THE EMBODIMENT

Figure 1:
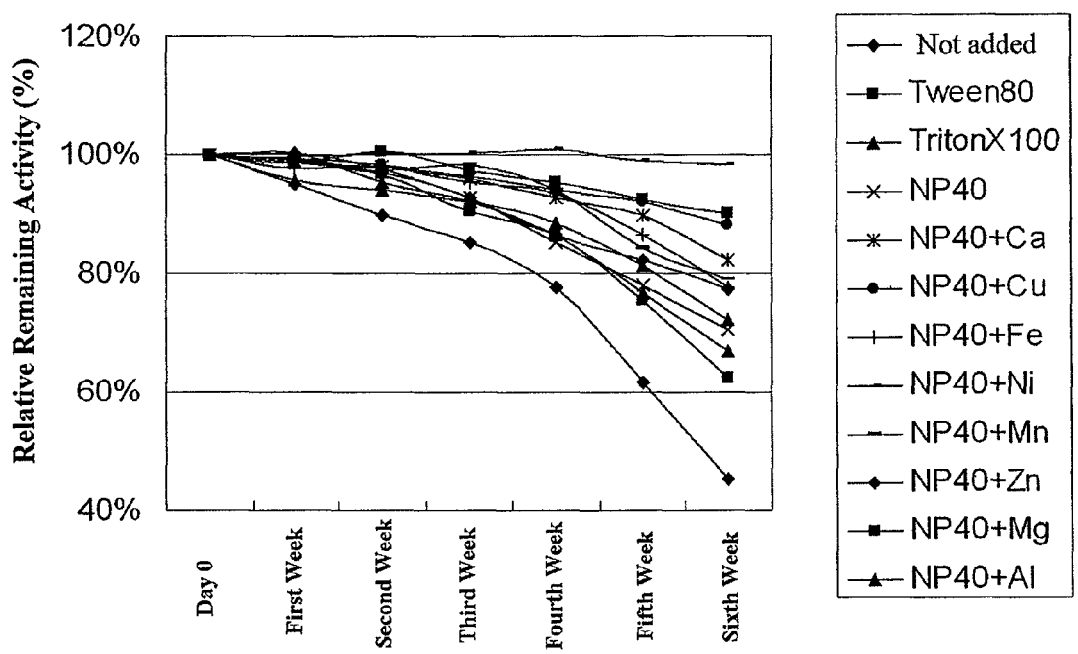
FIG. 1 is a graph wherein the influence of the types of a nonionic surfactant and a heavy metal ion on the stability of a tissue factor is shown in relative remaining activity.

The nonionic surfactant in this embodiment is not particularly limited insofar as it is a surfactant that does not dissociate an ion in an aqueous solution. Examples of such nonionic surfactants include octyl glucoside, peptyl thioglucoside, polyoxyethylene dodecyl ether, polyoxyethylene octyl phenyl ether, polyoxyethylene nonyl phenyl ether, polyoxyethylene fatty acid ester, sucrose fatty acid ester and polyoxyethylene sorbitan ester. Preferable examples include polyoxyethylene octyl phenyl ether and polyoxyethylene sorbitan ester. Particularly preferable examples include polyoxyethylene (9) octyl phenyl ether (trade name: NP-40), polyoxyethylene (10) octyl phenyl ether (trade name: Triton X-100) and polyoxyethylene (20) sorbitan monooleate (tradename: Tween 80).

The amount of the nonionic surfactant added is not particularly limited insofar as the measurement result of blood clotting ability by the reagent for measuring clotting time does not affect on diagnosis. For example, the concentration of the nonionic surfactant in the reagent for measuring clotting time is preferably 0.1 to 10 (v/v) %, more preferably 0.5 to 5 (v/v) %.

The nickel ion in this embodiment refers to a nickel ion present in the reagent for measuring clotting time. The nickel ion can be easily formed by adding a nickel salt to the reagent for measuring clotting time. The nickel salt includes, but not limited to, nickel sulfate, nickel chloride, nickel nitrate and nickel acetate.

The concentration of the nickel ion in the reagent for measuring clotting time is not particularly limited insofar as the measurement result of blood clotting ability by the reagent for measuring clotting time does not affect on diagnosis. For example, the concentration of the nickel ion is preferably 0.01 to 1.0 mM, more preferably 0.05 to 0.5 mM.

The tissue factor in this embodiment includes a natural-derived factor derived from a mammalian brain and placenta and a genetic recombinant tissue factor prepared by genetic recombination techniques. Preferable examples include tissue factors derived from a human, cattle, a rabbit and/or a monkey, and a genetic recombinant bovine tissue factor prepared from a silkworm pupa.

The tissue factor in this embodiment broadly means blood clotting factor III. The tissue factor in this embodiment includes an apoprotein tissue factor and thromboplastin that is a tissue factor having formed a complex with a phospholipid.

The recombinant bovine tissue factor from a silkworm pupa can be prepared for example in the following manner:
(1) A silkworm pupa infected with a recombinant baculovirus in which a cDNA encoding a bovine tissue factor has been integrated is disrupted in a buffer with a homogenizer to give a disruption solution.
(2) The disruption solution is filtered with a sterile gauze, followed by disrupting the disruption solution again with a homogenizer.
(3) The resulting disruption solution is centrifuged to recover a supernatant, thereby giving a solid component-free solution.
(4) A nonionic surfactant is added to, and incubated with, the solid component-free solution, thereby inactivating the baculovirus, to give a solution having a genetic recombinant bovine tissue factor solubilized therein.

The purified naturally-derived tissue factor, the genetic recombinant tissue factor or the like has not formed a complex with a phospholipid. Accordingly, when the tissue factor is used in a reagent for measuring clotting time, the tissue factor should be allowed to form a complex with a phospholipid. The method of forming a complex of the tissue factor and a phospholipid may be a method known in the art and is not particularly limited. For example, there is a method wherein a surfactant such as deoxycholate is used to form a lipid solution having a phospholipid dissolved therein, then the genetic recombinant tissue factor is added to this lipid solution, and the surfactant is removed by dialysis or the like.

The reagent for measuring clotting time in this embodiment is not particularly limited insofar as it is used in a blood clotting test of an extrinsic factor and common factor system. Examples include a prothrombin time measurement reagent and a reagent for measurement of a combined factor. The reagent is particularly preferably a reagent measuring blood clotting factors II, VII and/or X. The reagent for measuring clotting time in this embodiment encompasses a reagent kit composed of a plurality of reagents.

The blood clotting factor in the extrinsic factor system includes factor VII. The blood clotting factor in the common factor system includes factors X, V, II and I.

A buffer may be optionally added to the reagent for measuring clotting time. The type and concentration of the buffer are not particularly limited and may be suitably selected depending on the object etc. of the reagent for measuring clotting time. Specific examples of the buffer solution include HEPES, TRIPS, MOPS, PIPES, BISTRIS and Glycine. The concentration of the buffer is preferably 10 to 100 mM.

The pH of the reagent for measuring clotting time is not particularly limited and can be suitably regulated insofar as the ability thereof to measure clotting time is not affected. For example, the pH is preferably 5 to 9, more preferably 6 to 8.

The prothrombin time measurement reagent in this embodiment is not particularly limited insofar as it has a nonionic surfactant, a nickel ion, a tissue factor and a calcium ion, and simultaneously the tissue factor is coexistent with the nonionic surfactant and a nickel ion.

The prothrombin time measurement reagent can also be constituted as a prothrombin time measurement reagent kit comprising a first reagent containing a tissue factor, a nonionic surfactant and a nickel ion and a second reagent containing a calcium ion.

The combined factor measuring reagent in this embodiment is not particularly limited insofar as it has a nonionic surfactant, a nickel ion, a tissue factor, blood clotting factor V, fibrinogen and a calcium ion, and simultaneously the tissue factor is coexistent with the nonionic surfactant and a nickel ion.

The combined factor measuring reagent can also be constituted as a combined factor measuring reagent kit comprising a first reagent containing a tissue factor, a nonionic surfactant, a nickel ion, blood clotting factor V and fibrinogen and a second reagent containing a calcium ion.

As blood clotting factor V and fibrinogen, barium sulfate-adsorbed plasma can be used. The method of preparing barium sulfate-adsorbed plasma may be a method known in the art and is not particularly limited. For example, barium sulfate-adsorbed plasma can be prepared by a method of Owren et al. (One-stage Prothrombin Time Techniques (Thrombosis and Bleeding Disorders Theory and Method, 1971, pp. 92-97)). More specifically, the barium sulfate-adsorbed plasma can be prepared by adding about 10 to 30 (w/v) % of barium sulfate to bovine plasma, mixing it at room temperature for about 20 minutes, and then removing the barium sulfate. This adsorbed plasma is substantially free of at least clotting factors II, VII and X, and contains objective factor V and fibrinogen. Alternatively, purified products of blood clotting factor V and fibrinogen may be added to the reagent.

In preparation of the reagent for measuring clotting time, the order of adding the barium sulfate-adsorbed plasma, a calcium salt serving as a calcium ion source, a buffer etc. is not particularly limited. These ingredients may be added before or after formation of a tissue factor/phospholipid complex.

The reagent for measuring clotting time in this embodiment may be formed into a lyophilized reagent. The lyophilized reagent is not particularly limited insofar as the tissue factor is coexistent with the nonionic surfactant and a nickel ion upon dissolution in purified water or a buffer solution in use. For example, a nonionic surfactant and a nickel ion may be added to purified water or a buffer solution. Accordingly, it is not necessary that the tissue factor in a lyophilized state is coexistent with the nonionic surfactant and a nickel salt.

The method for stabilizing a tissue factor in this embodiment is not particularly limited insofar as a nonionic surfactant and a nickel ion are coexistent with the tissue factor. That is, the tissue factor can be stabilized insofar as a nonionic surfactant, a nickel ion and the tissue factor are in such a state as to be coexistent in solution.

The nonionic surfactant, nickel ion and tissue factor used in this method can be the same as the above mentioned nonionic surfactant, nickel ion and tissue factor.

EXAMPLES

Example 1

(Influence of the Types of a Nonionic Surfactant and a Heavy Metal Ion on the Stability of a Tissue Factor)

<Preparation of a Genetic Recombinant Bovine Tissue Factor>

A buffer solution (20 mM Tris-HCl, 150 mM sodium chloride, 10 mM benzamidine, 1 mM PMSF, 1 mM DDT, 1 mM EDTA, 1 mM EGTA, pH 7.5) was added in a volume of 10 mL/pupa to silkworm pupae infected with a recombinant baculovirus prepared by incorporating a bovine tissue factor-coding cDNA in a baculovirus, and the silkworm pupae were disrupted under cooling on ice with a polytron homogenizer (number of revolutions of 12000 rpm, 5 minutes), thereby giving a solution containing disrupted materials. This solution was filtered with a sterile gauze, thereby removing solid components, followed by disruption with a Teflon homogenizer (AS ONE, 10 strokes at a revolution number of 5000 rpm), to give a disruption solution.

The disruption solution was centrifuged (3000×g, 8° C., 10 minutes) to recover a supernatant as a solid component-free solution. 2 parts by volume of 10% nonionic surfactant were added to 8 parts by volume of the solid component-free solution, and the mixture was incubated at 30° C. for 3 hours, thereby inactivating the baculovirus and simultaneously solubilizing the genetic recombinant bovine tissue factor, to give a solution of the genetic recombinant bovine tissue factor.

The inactivation of the baculovirus was confirmed by examining the viral titer of the solid component-free solution treated with the nonionic surfactant by observing the presence or absence of viral infection on 96 wells by visual check under a microscope, according to the Reed-Muench method (Reed, L. J. and Muench, H.: Amer. J. Hyg., 27, 493 (1938)).

<Method of Measuring the Biological Activity of the Tissue Factor>

The bioactivity of the tissue factor was determined by measuring, as titer, the absorbance of the tissue factor in the following procedures based on Assay Sense Tissue Factor (TF) Chromogenic Activity Assay Kit (Assay Pro Kit) manufactured by Assay Pro. Measurement was carried out repeatedly 3 times to determine the average absorbance.

(1) A constituent reagent, rhTF, FVII, FVIIa Substrate, in a tissue factor synthetic substrate measurement kit (hereinafter referred to as TF assay kit) manufactured by Assay Pro is prepared according to instructions of the kit.
(2) A TF standard solution (1000 pM) is diluted serially with a diluent to prepare ×1, ×2, ×4, ×8 and ×16 dilution series and a blank (diluent only).
(3) A test sample (tissue factor solution) is diluted 100-fold with a separate diluent.
(4) A dilution (50 μL) is accurately pipetted into each well of a microtiter plate (manufactured by Nunc).
(5) An FVII solution (25 μL) is accurately pipetted to each well.
(6) Then, 20 μl of the previously prepared TF standard solution and 20 μl of the previously prepared test sample are pipetted to each well, and the microplate is agitated for 10 seconds.
(7) The microplate is covered with a protective film and incubated at 37° C. for 30 minutes in a plate reader (VERSA Max reader, Molecular Device).
(8) The protective is released, and the synthetic substrate reagent (25 μL) is accurately pipetted into each well.
(9) The sample is reacted at 37° C. for 60 minutes and measured for its absorbance at 405 nm in the plate reader (VERSA Max reader, Molecular Device).
(10) The absorbance of the test sample at 405 nm is subtracted from the absorbance of the blank (diluent) to determine the corrected absorbance of the test sample.

<Preparation of Sample Solutions Different in the Type of Nonionic Surfactant>

As solutions of the genetic recombinant bovine tissue factor expressed in silkworm pupae as the host, the following solutions were prepared and stored at 8° C.:

(1) a solution extracted with a nonionic surfactant-free buffer (20 mM Tris-HCl, 150 mM sodium chloride, 10 mM benzamidine, 1 mM PMSF, 1 mM DDT, 1 mM EDTA, 1 mM EGTA, pH 7.5),
(2) a solution extracted with a buffer containing 2% NP-40,
(3) a solution extracted with a buffer containing 2% Triton-X100, and
(4) a solution extracted with a buffer containing 2% Tween 80.

<Preparation of Sample Solutions Different in the Type of Heavy Metal Ion>

As the type of heavy metal ion, a divalent metal ion such as Ni sulfate, Mg chloride, Ca chloride, Cu sulfate, Zn chloride, Fe chloride or Mn chloride or a trivalent metal ion such as Al chloride was added at a final concentration of 0.5 mM to each solution (5 mL), collected in a sample cup, of the genetic recombinant bovine tissue factor extracted with a buffer containing 2% NP-40, and then each sample was stored at 8° C.

<Measurement of the Biological Activity of the Tissue Factor>

The biological activity of each sample solution with time was determined by measuring its absorbance at 405 nm with the above-mentioned Assay Pro kit. The result of the relative remaining activity (relative to the biological activity (=100%) on Day 0) determined on the basis of the measurement result of the absorbance is shown in Table 1 and FIG. 1.

TABLE 1

| | Day 0 | First Week | Second Week | Third Week | Fourth Week | Fifth Week | Sixth Week |
|---|---|---|---|---|---|---|---|
| Not added | 100% | 95% | 90% | 85% | 78% | 62% | 45% |
| Tween80 | 100% | 99% | 97% | 90% | 86% | 75% | 62% |
| TritonX100 | 100% | 100% | 95% | 92% | 87% | 77% | 67% |
| NP40 | 100% | 99% | 97% | 93% | 85% | 78% | 70% |
| NP40 + Ca | 100% | 99% | 98% | 96% | 93% | 90% | 82% |
| NP40 + Cu | 100% | 99% | 98% | 96% | 94% | 92% | 88% |
| NP40 + Fe | 100% | 98% | 98% | 95% | 93% | 86% | 78% |
| NP40 + Ni | 100% | 100% | 100% | 100% | 101% | 99% | 98% |
| NP40 + Mn | 100% | 99% | 97% | 98% | 94% | 84% | 79% |
| NP40 + Zn | 100% | 100% | 98% | 93% | 87% | 82% | 77% |
| NP40 + Mg | 100% | 99% | 101% | 97% | 95% | 92% | 90% |
| NP40 + Al | 100% | 96% | 94% | 92% | 89% | 81% | 72% |

As is evident from Table 1 and FIG. 1, the specific activity of the genetic recombinant bovine tissue factor solution extracted with the buffer only was reduced with time, and reduced in the third week to 85% and in the sixth week to 45%. The specific activity of the genetic recombinant bovine tissue factor solution extracted with the buffer containing 2% nonionic surfactant (NP-40, Triton-X100, or Tween 80) was reduced to about 90% in the third week and to about 60 to 70% in the sixth week. The specific activity of the other samples in the presence of heavy metal ions was recognized to be kept at about 90 to 100% in the third week and at 70 to 98% in the sixth week. The specific activity of the solution containing 2% NP-40 and a nickel ion was kept at 100% in the third week and at 98% in the sixth week.

It was thus revealed that the biological activity of the tissue factor can be maintained for a longer period in the sample solution containing the nonionic surfactant NP-40 and a nickel ion than in the other sample solutions.

Example 2

(Influence of the Concentration of a Nickel Ion on the Stability Of the Tissue Factor Nickel sulfate was not added (0 mM) or added at a concentration of 0.025 mM, 0.05 mM, 0.1 mM, 0.2 mM, 0.3 mM, 0.4 mM or 0.5 mM to a solution (5 mL), collected in a sample cup, of the genetic recombinant bovine tissue factor extracted with the buffer containing 2% NP-40, and after the sample cup was capped, each sample was stored for 6 weeks in a cool box at 8° C. As the control, the genetic recombinant bovine tissue factor solution (5 mL) extracted with the buffer only was used.

The biological activity of the tissue factor in each sample at each concentration was measured with the above-mentioned Assay Pro kit in the same manner as in Example 1. The results of the relative remaining activity are shown in Table 2 and FIG. 2.

TABLE 2

|  | Day 0 | First Week | Second Week | Third Week | Fourth Week | Fifth Week | Sixth Week |
|---|---|---|---|---|---|---|---|
| 0 mM | 100% | 99% | 97% | 93% | 85% | 78% | 70% |
| 0.025 mM | 100% | 97% | 98% | 97% | 96% | 93% | 91% |
| 0.05 mM | 100% | 102% | 96% | 98% | 99% | 95% | 94% |
| 0.1 mM | 100% | 100% | 100% | 100% | 99% | 100% | 100% |
| 0.2 mM | 100% | 101% | 98% | 101% | 97% | 98% | 100% |
| 0.3 mM | 100% | 99% | 100% | 99% | 99% | 101% | 98% |
| 0.4 mM | 100% | 99% | 100% | 100% | 99% | 98% | 100% |
| 0.5 mM | 100% | 99% | 100% | 101% | 99% | 100% | 101% |

Figure 2:
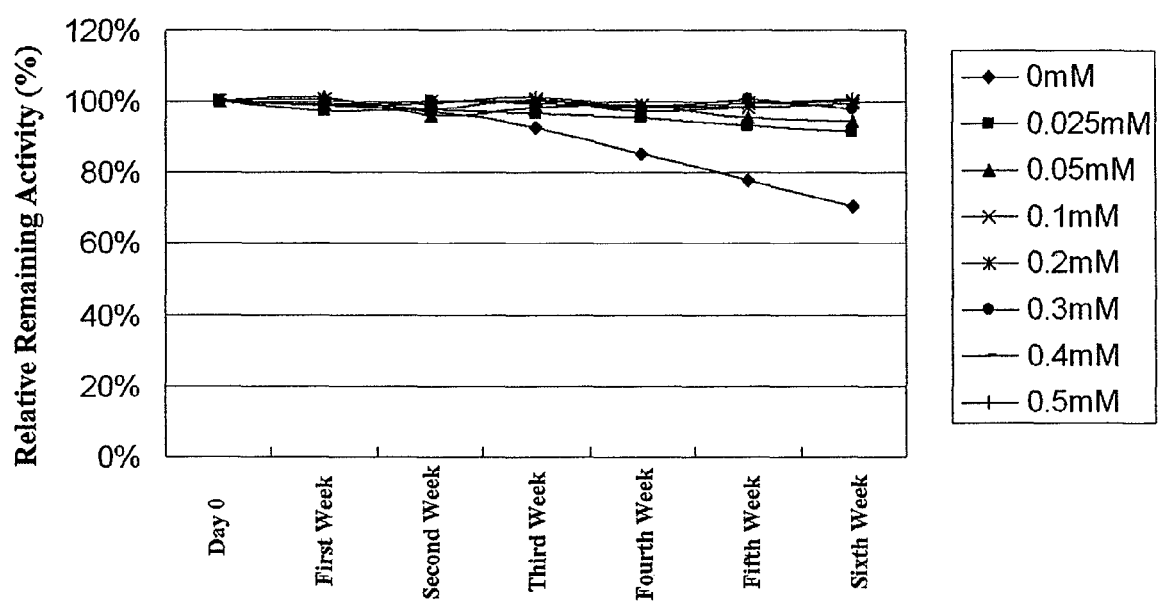
FIG. 2 is a graph wherein the influence of the concentration of a nickel ion on the stability of a tissue factor is shown in relative remaining activity.

As is evident from Table 2 and FIG. 2, the specific activity of the genetic recombinant bovine tissue factor solution extracted with the buffer only was reduced with time, and reduced to 85% in the third week and to 45% in the sixth week. On the other hand, the specific activity of the genetic recombinant bovine tissue factor solution containing nickel at a concentration of 0.025 mM was kept at up to about 97% in the third week and at up to about 91% in the sixth week. The specific activity of the solution containing nickel at a concentration of 0.1 mM or more was recognized to be 100% in the third week and 100% in the sixth week.

It was thus revealed that the biological activity of the tissue factor can be maintained for a longer period in the sample solutions containing 0.25 mM or more, preferably 0.1 mM or more, nickel ion than in the sample solution containing the nonionic surfactant NP-40 only.

Example 3

(Influence on the Stability of the Tissue Factor Stored in a Frozen State)

A solution of the genetic recombinant bovine tissue factor extracted with a buffer (20 mM Tris-HCl, 150 mM sodium chloride, 10 mM benzamidine, 1 mM PMSF, 1 mM DDT, 1 mM EDTA, 1 mM EGTA, pH 7.5), a solution of the genetic recombinant bovine tissue factor extracted with the buffer containing 2% NP-40, or a solution of the genetic recombinant bovine tissue factor extracted with the buffer containing 2% NP-40 and then mixed with 0.1 mM nickel sulfate, was collected in a 5-mL sample cup which was then capped and stored in a refrigerator (8° C.) and in a freezer (−20° C., −35° C., −80° C.). The biological activity of the tissue factor under these conditions was measured with the above-mentioned Assay Pro kit in the same manner as in Example 1. The results are shown in Table 3 and FIG. 3.

TABLE 3

|  |  | Month 0 | First month | Third month | Sixth month |
|---|---|---|---|---|---|
| Buffer | Buffer in a freezer (−35° C.) | 100% | 94% | 68% | 33% |
| Buffer + NP40 | Buffer + NP40 in a freezer (−35° C.) | 100% | 92% | 81% | 64% |
| Buffer + NP40 + Ni | Buffer + NP40 + Ni in a refrigerator (8° C.) | 100% | 96% | 90% | 83% |
|  | Buffer + NP40 + Ni in a freezer (−20° C.) | 100% | 102% | 103% | 96% |
|  | Buffer + NP40 + Ni in a freezer (−35° C.) | 100% | 103% | 104% | 102% |
|  | Buffer + NP40 + Ni in a freezer (−80° C.) | 100% | 94% | 97% | 99% |

Figure 3:
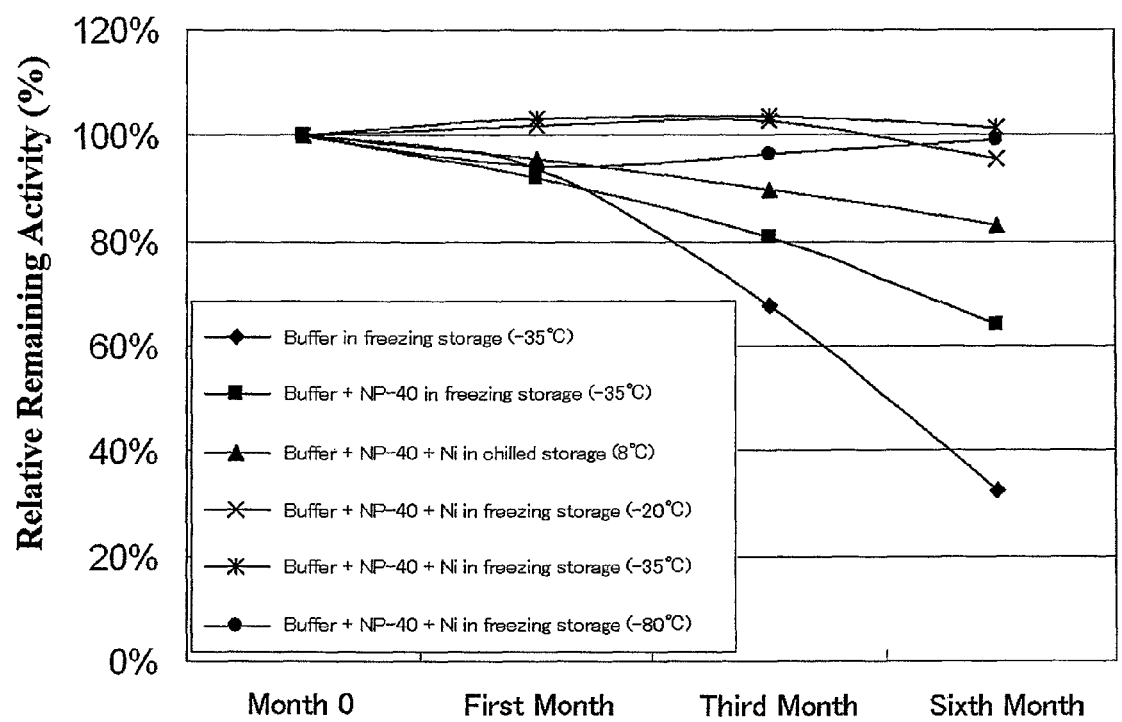
FIG. 3 is a graph wherein the influence of a nonionic surfactant and a nickel ion on the stability of a tissue factor stored in a frozen state is shown in relative remaining activity.

As is evident from Table 3 and FIG. 3, it was confirmed that the samples containing NP-40 and a nickel ion maintained a stable biological activity in freezing storage in any storage periods. Further, the results indicated that the stability of the sample containing NP-40 and a nickel ion in chilled storage at 8° C. was higher than that of the sample containing NP-40 only in freezing storage at −35° C.

Example 4

(Stability of the Tissue Factor in a Combined Clotting Factor Measuring Reagent)

<Preparation of a Recombinant Bovine Tissue Factor-phospholipid Complex>

0.4 g of Basis Soybean Lecithin (Nisshin Oil Mills, Ltd.) was dissolved in 0.25% sodium deoxycholate (DOCNa) (20 mL). The mixture was completely dissolved at room temperature under stirring with a rotator, and 0.1 g of 1,2-oleyl-sn-glycero-3-phosphoethanolamine (DOPE) and 0.3 g of 1,2-dioleyl-sn-glycero-3-phospho-L-serine (DOPS) (both available from Avanti polar lipid, Inc.) were suspended therein to prepare a phospholipid solution.

To 37.5 mL of this phospholipid solution were added 5 mL of 0.5 M nickel chloride solution, 5.0 mL of 10 mM HEPES buffer (pH 7.3), and the genetic recombinant bovine tissue factor-containing solution (2.5 mL), and the mixture was stirred for 30 seconds with a vortex. After stirring, the mixture was reacted at 37° C. for 15 minutes with a BRANSON #2210 ultrasonic device and then left at 37° C. for 1 hour. The solution was transferred into a dialysis membrane (cellulose tube for dialysis, Sanko Junyaku Co., Ltd.) and dialyzed 3 times against 10 mM HEPES (containing 0.15M sodium chloride), pH 7.3, and after dialysis, the solution in the dialysis tube was obtained as a bovine tissue factor-phospholipid complex-containing solution (bovine tissue factor-phospholipid complex-containing solution).

2% and 0.1 mM, respectively, then stored in a refrigerator (8° C.) and in a freezer (−20° C., −35° C., −80° C.), and examined for its reagent sensitivity in a blood clotting test. As the control, the combined factor reagent to which nickel sulfate had not been added was prepared.

In the sensitivity and reproducibility test, the clotting time (sec) of standard plasma was measured with a fully automatic blood clotting analyzer Coagurex 800 (Shimadzu Corporation), and then the sample after diluted 8-fold with physiological saline was measured in triplicate. As the standard plasma, Coagutrol N (Sysmex Corporation) was used. For calculation of ISI value, an AK Calibrant (Sysmex Corporation) was used as a sample, and the ISI value of the reagent under the respective conditions was calculated. The test results are shown in Table 4.

TABLE 4

| Sample | Stored with no additive in refrigerator (2% NP40 added) | | Stored in refrigerator (0.1 mM Ni added, 2% NP-40 added) | | Stored for 6 months in freezer (0.1 mM Ni added, 2% NP-40 added) | | |
|---|---|---|---|---|---|---|---|
| | Day 0 | Third Week | First Week | Third Week | −20° C. | −35° C. | −80° C. |
| Standard plasma (×1) | 33.3 | 41.5 | 32.4 | 32.8 | 33.6 | 34.1 | 33.9 |
| Standard plasma (×8) | 85.3 | 165.7 | 86.8 | 87.2 | 85.1 | 87.2 | 85.8 |
| ISI value | 0.93 | 1.16 | 0.95 | 0.94 | 0.96 | 0.96 | 0.94 |
| Specific activity (%) | 100% | 85% | 100% | 95% | 96% | 102% | 99% |

<Preparation of a Combined Factor (Factors II, VII and X) Measuring Reagent>

(1) Preparation of Barium Sulfate-adsorbed Plasma

To citric acid-containing bovine plasma were added barium sulfate in an amount of 30 w/v % relative to the bovine plasma and physiological saline in an amount of 20 v/v % relative to the bovine plasma, and the mixture was stirred for 60 minutes with a rotator.

This mixture was centrifuged at 4° C. for 5000 rpm for 15 minutes to recover a supernatant. Barium sulfate in an amount of 30 w/v % relative to the supernatant was added little by little to the supernatant, whereby factors II, VII, IX and X in the plasma were adsorbed onto the barium sulfate. Thereafter, the sample was centrifuged to recover a supernatant. The recovered supernatant was introduced into a dialysis tube (cellulose tube for dialysis, Sanko Junyaku Co., Ltd.) and dialyzed against physiological saline at 2 to 8° C. After dialysis, the solution in the dialysis tube was filtered through a 0.45-μm filter to give a filtrate as barium sulfate-adsorbed plasma.

(2) Preparation of a Combined Factor (Factors II, VII and X) Measuring Reagent

The bovine tissue factor-phospholipid complex-containing solution prepared above, the barium sulfate-adsorbed plasma, and 40 mM HEPES buffer (pH 7.3, containing 4 mM calcium lactate) were mixed at a ratio of 1:2:1, to prepare a combined factor reagent (reagent for measurement of factors II, VII and X).

<Evaluation of the Reagent Sensitivity of the Combined Factor Reagent in Long Storage>

The combined factor reagent (reagent for measuring factors II, VII and X) was prepared by adding P-40 and nickel sulfate to a crude extracted genetic recombinant bovine tissue factor-containing solution while being at concentrations of As is evident from Table 4, the reagent sensitivity of the combined factor reagent to which NP-40 and nickel sulfate had been added, when stored for 4 weeks in a refrigerator and for 6 months in a freezer, was in the range of 32 to 35 seconds with the standard plasma, that is, a clotting time in the normal range. The ISI value was in the range of 0.9 to 1.0, indicating sufficient reagent sensitivity as a reagent for clinical examination.

On the other hand, the reagent sensitivity of the control to which nickel sulfate had not been added, when stored for 4 weeks in a refrigerator, was 40 seconds or more with the standard plasma, or 100 seconds or more with the 1:8 diluted plasma, indicating performance not practical as a reagent for clinical examination.

<Evaluation of Measurement Accuracy of the Combined Factor Reagent in Long Storage>

The combined factor reagent and control prepared in evaluation of the regent sensitivity described above were stored in a refrigerator (8° C.) and in a freezer (−20° C., −35° C., −80° C.), and examined in a measurement accuracy test as a blood clotting test.

The measurement accuracy test was carried out repeatedly 5 times by using a normal-range control plasma Coagutrol I (Sysmex Corporation) and an abnormal-range control plasma Coagutrol IIX (Sysmex Corporation). The results of clotting time (sec) obtained by using Coagutrol I are shown in Table 5, and the results of clotting time (sec) obtained by using Coagutrol IIX are shown in Table 6.

TABLE 5

| Normal-range sample | Stored with no additive in refrigerator (2% NP-40 added) | | Stored in refrigerator (0.1 mM Ni added, 2% NP-40 added) | | Stored for 6 months in freezer (0.1 mM Ni added, 2% NP-40 added) | | |
|---|---|---|---|---|---|---|---|
| | Day 0 | Third Week | First Week | Third Week | −20° C. | −35° C. | −80° C. |
| Normal-range control plasma (Coagutrol I) | 34.5 | 40.5 | 34.9 | 35.7 | 35.2 | 35.4 | 35.1 |
| | 34.1 | 41.3 | 34.9 | 35.2 | 35.2 | 35.7 | 35.3 |
| | 34.6 | 40.9 | 34.4 | 35.3 | 35.1 | 35.6 | 35.2 |
| | 34.6 | 41.3 | 34.7 | 35.2 | 35.1 | 35.6 | 35.3 |
| | 34.4 | 41.8 | 34.6 | 35.3 | 35.3 | 35.4 | 35.4 |
| Mean value | 34.4 | 41.2 | 34.7 | 35.3 | 35.2 | 35.5 | 35.3 |
| Standard deviation | 0.207 | 0.488 | 0.212 | 0.207 | 0.084 | 0.134 | 0.114 |
| CV value | 0.60% | 1.18% | 0.61% | 0.59% | 0.24% | 0.38% | 0.32% |

TABLE 6

| Abnormal-range sample | Not added (containing NP-40) | | Refrigerated (0.1 mM Ni + NP-40) | | Frozen (0.1 mM Ni + NP-40) | | |
|---|---|---|---|---|---|---|---|
| | Day 0 | Third Week | First Week | Third Week | −20° C. | −35° C. | −80° C. |
| Abnormal-range control plasma (Coagutrol IIX) | 45.5 | 75.6 | 44.8 | 45.5 | 45.2 | 46.7 | 46.6 |
| | 46.2 | 77.9 | 44.9 | 45.2 | 45.2 | 46.9 | 46.3 |
| | 46.2 | 76.1 | 44.9 | 45.1 | 45.4 | 46.7 | 46.1 |
| | 45.7 | 77.2 | 44.8 | 45.0 | 45.4 | 46.4 | 46.0 |
| | 46.3 | 78.5 | 45.0 | 44.9 | 45.8 | 46.9 | 46.1 |
| Mean value | 46.0 | 77.1 | 44.9 | 45.1 | 45.4 | 46.7 | 46.2 |
| Standard deviation | 0.356 | 1.210 | 0.084 | 0.230 | 0.245 | 0.205 | 0.239 |
| CV value | 0.77% | 1.57% | 0.19% | 0.51% | 0.54% | 0.44% | 0.52% |

As is evident from Tables 5 and 6, the control to which nickel sulfate had not been added showed a high CV value of reproducibility in chilled storage for 3 weeks, and did not satisfy practical reagent performance similarly to reagent sensitivity. On the other hand, the combined factor reagent prepared by adding both NP-40 and nickel sulfate, when stored for 3 weeks in a refrigerator and stored for 6 months in a freezer, was recognized to show measurement accuracy as within-run reproducibility showing a CV value of less than 1%.

From the results described above, it was revealed that the stability of the tissue factor in solution is improved by the presence of a nonionic surfactant and a nickel ion. From the foregoing, the tissue factor-containing reagent for measuring clotting time, etc., can be stored for a longer period than prior art.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is:

1. A method for stabilizing a tissue factor in a liquid reagent to maintain its biological activity during storage comprising the steps of coexisting a nonionic surfactant and a nickel ion with the tissue factor in water, and storing the liquid reagent for at least a week before use.

2. The method according to claim 1, wherein the nonionic surfactant is at least one selected from the group consisting of polyoxyethylene octyl phenyl ether and polyoxyethylene sorbitan ester.

3. The method according to claim 1, wherein the nickel ion is a nickel ion derived from at least one selected from the group consisting of nickel sulfate, nickel chloride, nickel nitrate and nickel acetate.

4. The method according to claim 1, wherein the tissue factor is derived from at least one selected from the group consisting of a human, cattle, a rabbit and a monkey.

5. The method according to claim 1, wherein the tissue factor is a genetic recombinant tissue factor prepared from a silkworm pupa.

6. A method for measuring clotting time, comprising steps of: mixing a plasma sample and a liquid reagent for measuring clotting time comprising water, a nonionic surfactant, a nickel salt and a tissue factor, wherein the liquid reagent has been stored for at least a week before being mixed with the plasma sample, and wherein the coexistence of the nonionic surfactant and nickel salt with the tissue factor in water during storage serves to stabilize the tissue factor by maintaining its biological activity; and measuring the clotting time of the mixture.

7. The method according to claim 6, wherein the nonionic surfactant is at least one selected from the group consisting of polyoxyethylene octyl phenyl ether and polyoxyethylene sorbitan ester.

8. The method according to claim 6, wherein the nickel salt is at least one selected from the group consisting of nickel sulfate, nickel chloride, nickel nitrate and nickel acetate.

* * * * *